(12) United States Patent
Wieland (10) Patent No.: US 10,799,270 B2
(45) Date of Patent: Oct. 13, 2020

(54) CONICAL END CAP FOR INTRAMEDULLARY NAIL

(71) Applicant: Stryker European Holdings I, LLC, Kalamazoo, MI (US)

(72) Inventor: Manfred Wieland, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/395,286

(22) Filed: Dec. 30, 2016

(65) Prior Publication Data

US 2017/0143388 A1    May 25, 2017

Related U.S. Application Data

(63) Continuation-in-part of application No. PCT/EP2015/065251, filed on Jul. 3, 2015.

(30) Foreign Application Priority Data

Jul. 3, 2014    (WO) .................. PCT/EP2014/064232

(51) Int. Cl.
| | |
|---|---|
| *A61B 17/68* | (2006.01) |
| *A61B 17/72* | (2006.01) |
| *A61B 17/86* | (2006.01) |
| *A61B 17/84* | (2006.01) |

(52) U.S. Cl.
CPC ............ *A61B 17/685* (2013.01); *A61B 17/72* (2013.01); *A61B 17/7283* (2013.01); *A61B 17/846* (2013.01); *A61B 17/86* (2013.01); *A61B 17/8625* (2013.01)

(58) Field of Classification Search
CPC ... A61B 17/685; A61B 17/283; A61B 17/846; A61B 17/86; A61B 17/863; A61B 17/7283
See application file for complete search history.

(56) References Cited

U.S. PATENT DOCUMENTS

| | | | |
|---|---|---|---|
| 3,133,578 A | 5/1964 | Moskovitz | |
| 3,364,807 A | 1/1968 | Holton | |
| 4,167,355 A * | 9/1979 | Hansson | ................ F16B 2/065 403/374.3 |
| 4,917,555 A | 4/1990 | Taubert | |
| 5,340,254 A | 8/1994 | Hertel et al. | |

(Continued)

FOREIGN PATENT DOCUMENTS

| | | |
|---|---|---|
| CN | 102188282 A | 9/2011 |
| DE | 20316200 U1 | 12/2003 |

(Continued)

OTHER PUBLICATIONS

PCT/EP2015/065251 International Search Report dated Sep. 18, 2015.

(Continued)

*Primary Examiner* — Ellen C Hammond
*Assistant Examiner* — Tara Rose E Carter
(74) *Attorney, Agent, or Firm* — Lerner, David, Littenberg, Krumholz & Mentlik, LLP (57) ABSTRACT

An end cap is provided comprising a head with a tool engagement portion and a shaft with a tip, wherein the shaft comprises a threaded conical portion starting from the tip and extending in a direction to the head. The thread may be provided with a constant pitch, i.e. with a constant distance between the turns of the thread.

20 Claims, 7 Drawing Sheets

(56) References Cited

U.S. PATENT DOCUMENTS

| | | | |
|---|---|---|---|
| 5,827,030 A | 10/1998 | Dicke | |
| 6,152,666 A | 11/2000 | Walther et al. | |
| 6,235,031 B1* | 5/2001 | Hodgeman | A61B 17/744 606/64 |
| 6,450,748 B1 | 9/2002 | Hsu | |
| 6,508,820 B2 | 1/2003 | Bales | |
| 6,527,775 B1 | 3/2003 | Warburton | |
| 7,021,877 B2 | 4/2006 | Birkelbach et al. | |
| 9,173,042 B2 | 10/2015 | Jinton et al. | |
| 2001/0014262 A1 | 8/2001 | Friederich et al. | |
| 2005/0277936 A1* | 12/2005 | Siravo | A61B 17/72 606/62 |
| 2007/0219636 A1* | 9/2007 | Thakkar | A61B 17/1721 623/18.11 |
| 2007/0269288 A1* | 11/2007 | Palm | F16B 25/0021 411/386 |
| 2011/0200410 A1* | 8/2011 | Konagaya | F16B 35/047 411/412 |
| 2012/0330313 A1* | 12/2012 | Grady | A61B 17/7225 606/64 |
| 2013/0211522 A1* | 8/2013 | Weiss | A61B 17/8095 623/16.11 |

FOREIGN PATENT DOCUMENTS

| | | |
|---|---|---|
| DE | 102004034246 A1 | 2/2006 |
| EP | 2364657 A1 | 9/2011 |
| WO | 2014015942 A1 | 1/2014 |

OTHER PUBLICATIONS

PCT/EP2014/064232 International Search Report dated Mar. 5, 2015.

* cited by examiner

Prior Art

Prior Art

CONICAL END CAP FOR INTRAMEDULLARY NAIL

CROSS-REFERENCE TO RELATED APPLICATIONS

The present application is a continuation of International Application No. PCT/EP2015/065251 filed Jul. 3, 2015, published in English as WO 2016/001427 A1, which is a continuation in part of International Application No. PCT/EP2014/064232, published in English as WO 2016/000784 A1, filed Jul. 3, 2014, the disclosures of which are incorporated herein by reference.

BACKGROUND OF THE INVENTION

The invention relates to an implant. In particular, the invention relates to an end cap for use with an intramedullary nail. An implant and particularly a bone implant include a portion or section or end which is adapted to be firstly introduced into a body during an implantation. Such a portion or section or end is usually referred to as leading portion or leading section or leading end. Consequently, an opposite portion or section or end of the implant is adapted to be finally introduced, wherein this portion or section or end may additionally be configured for an engagement of a tool for inserting the implant into the body. Such a portion or section or end is usually referred to as trailing portion or trailing section or trailing end.

A bone implant may be a pin or a nail or screw. A bone nail may be an intramedullary nail, for example a femur nail, a humerus nail or a tibia nail. A bone screw may be a screw for fixing fragments of a bone fracture or may be a locking screw for locking a bone nail in the bone.

However, due to the anatomical variation of bones it may happen that the trailing end of a bone implant sticks out of a bone after implant placement. The trailing end of the implant may act as an interface towards a target or aiming device. In order to create a solid fixation nails may be provided with grooves in order to fit pegs on the post of the target device for accurate alignment, for sufficient fixation, and for controlling the forces applied during implant insertion and removal.

It may occur that patients complain about pain after surgery in this area, especially when the implant is sticking out of the bone. This pain may be caused by sharp edges at the trailing end of the implant. Such edges may cause irritations and/or injuries of the surrounding soft tissue.

On the other hand, the trailing end of a bone nail may be arranged within a bone, i.e. under a bone surface, after an implantation. In such case, bone tissue may grow over the trailing edges of the bone nail resulting in difficulties to explant the bone nail after healing of a treated bone fracture.

To reduce these problems, an end cap in form of a small screw may be inserted into the trailing end of the implant, with the screw having a screw head with a length and smooth and rounded edges.

Figure 1:
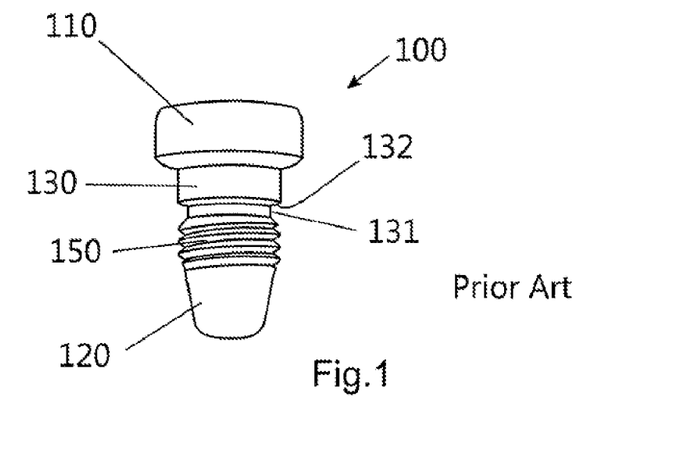
FIG. 1 shows an end cap according to the prior art.

FIG. 1 shows an end cap in accordance with the prior art. The end cap 100 comprises a head 110, a conical tip portion, a cylindrical portion 150 with an outer thread and an intermediate portion 130. A clearance groove 131 is provided between the thread portion 150 and intermediate portion 130 forming a shoulder 132. The conical tip portion 120 is formed with a smooth outer surface and a rounded tip.

Figures 2A, 2B, 2C, 2D:
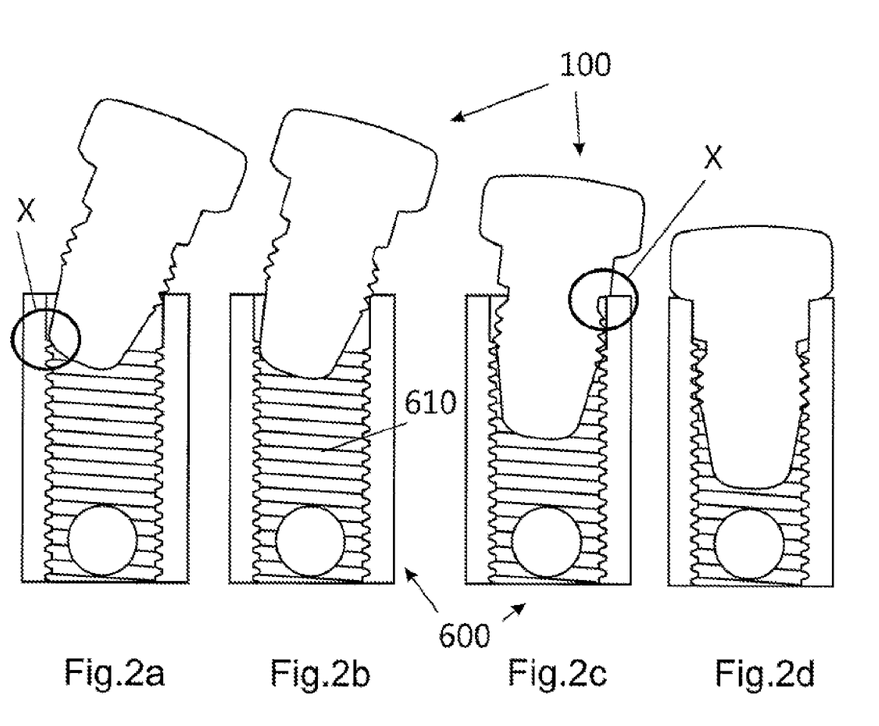
FIGS. 2a-2d show a sequence illustrating an introduction of the prior art end cap of FIG. 1 into a threaded trailing end of a bone nail.

In the sequence of FIGS. 2a-2d, an introduction of an end cap of FIG. 1 is illustrated. In FIG. 2a, the end cap 100 is tilted relative to the axis of the inner thread 610 in the bone nail 600. Such an angled introduction may particularly occur as the introduction of the end cap is performed more or less blindly, keeping in mind that the bone nail is already introduced into a bone (not shown) and the actual orientation of the axis of the bone nail is not recognizable. As indicated with the circle denoted with X, the front end 120 of the end cap will abut the first turn of the inner thread 610, impeding the introduction of end cap 100.

Before the outer threads of the end cap engage with the inner threads 610 of the bone nail 600, shoulder 132 at the intermediate section created by the clearance groove may further hinder an introduction of the end cap 100, as indicated by the circle denoted with X in FIG. 2c.

Figure 11:
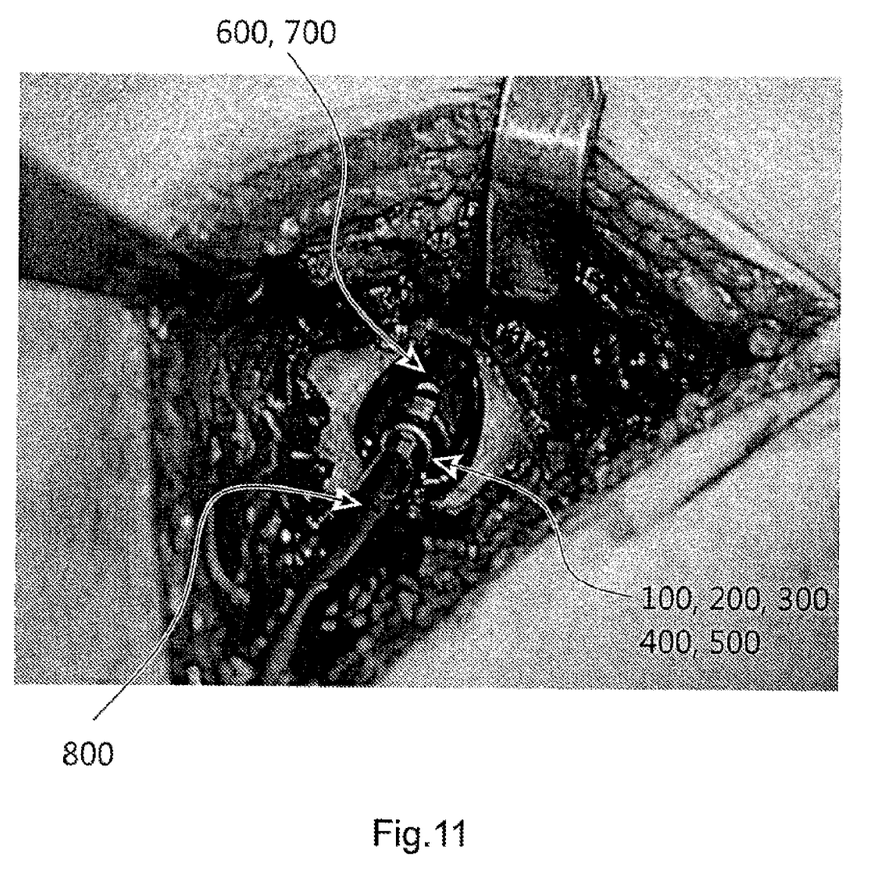
FIG. 11 is an image of an end cap introduction during surgery.

Therefore, it may be difficult to align the screw axis to an axis of an inner thread in the trailing end of the implant when introducing such a small screw into an implant which is already inserted into a bone and an axis of which is thus not clearly recognizable, i.e. visible, as can be seen in FIG. 11. Consequently, a small screw as an end cap may easily tilt during insertion.

BRIEF SUMMARY OF THE INVENTION

An object may be defined as providing an end cap for an implant, wherein an introduction of the end cap into a trailing end of an implant is facilitated.

This is achieved by the end cap according to the independent claim. Further embodiments are described in the dependent claims.

In general, an end cap comprises a head with a tool engagement portion and a shaft with a tip, wherein the shaft comprises a threaded conical portion starting from the tip and extending in a direction to the head. The thread may be provided with a constant pitch, i.e. with a constant distance between the turns of the thread. In other words, the distance between each of two adjacent turns of the thread is the same, when measured in a longitudinal direction of the end cap.

In accordance with an embodiment, the shaft has a longitudinal axis and the thread is provided on at least a portion of the shaft, wherein the thread comprises a first end adjacent the tip of the shaft, a first conical section, a second conical section and a second end, wherein the first conical section extends between the first end and the second conical section.

The first conical section is defined by a first cone with a first angle between its cone surface and the longitudinal axis, and the second conical section is defined by a second cone with a second angle between its cone surface and the longitudinal axis. The first angle may differ from the second angle. According to an embodiment, the first angle of the first conical section is smaller than the second angle of the second conical section.

According to an embodiment, the threaded portion may comprise a third section between the second conical section and the second end of the threaded portion, wherein the third section of the threaded portion defines a third cone with a third angle between its cone surface and the longitudinal axis, wherein the third angle differs from the first angle and differs also from the second angle. For example, the third angle may be smaller than the first angle as well as smaller than the second angle.

It is noted that in this disclosure, a cone surface of a threaded cone is to be understood as a virtual surface including the outer line of the thread formed by the major or outside diameter of the threads. That is, the cone surface virtually encloses the threads.

According to an embodiment, the thread at the shaft of the end cap may comprise a thread profile defining a centre axis between two adjacent tooth flanks, wherein the centre axis of the thread profile is perpendicular to the surface of the conical portion. Alternatively, the centre axis of the thread profile may be perpendicular to the longitudinal axis of the conical portion. It will be understood that the centre axis of the thread profile may also be in the middle or at any other angle between the mentioned alternative centre axes.

According to an embodiment, the first conical portion of the shaft of the end cap may define an angle of between 4° and 12° to a longitudinal axis of the end cap. Preferably, the first angle of the first conical section may be between 5° and 9°. For example, the conical portion may define an angle of 7° to the longitudinal axis. On the other hand, the second conical section may have a second angle between 15° and 30°, preferably between 20° and 25°. For example, the second angle may be 22.5°.

In general, a thread may be described by a major diameter and a minor diameter. The major diameter of a thread is the larger of two extreme diameters delimiting the height of the thread profile, as a cross-sectional view is taken in a plane containing the axis of the threads. The minor diameter is the lower extreme diameter of the thread. Major diameter minus minor diameter, divided by two, equals the height of the thread. It will be understood that a nominal diameter of an outer thread will actually differ from the major diameter of the thread to provide a clearance between the outer thread and a corresponding inner thread. Without such a clearance, the threads would not be able to move relative to each other.

According to an embodiment, the thread at the shaft of the end cap may have a maximal outer diameter, i.e. a maximal major diameter adjacent to the head, which diameter corresponds to a nominal diameter of an inner thread of an implant. For example, the maximal major diameter of the thread may be 8 mm. A screw with an outer diameter of 8 mm should fit into an inner thread with a nominal diameter of 8 mm, i.e. with a maximal inner diameter of the inner thread of slightly more than 8 mm, i.e. of for example 8.1 mm. It is noted that the thread at the conical portion may have at least one turn adjacent the head of the end cap with the maximal outer diameter.

According to another embodiment, the threaded portion comprises a further section between the second conical section and the second end of the threaded portion, wherein the further section of the threaded portion may be cylindrical. In other words, a cylindrical section may start from the second conical section and may extend in a direction to the head, wherein the thread continues with a constant diameter on the cylindrical section. That is, the thread according to this embodiment may have more than one turn of the thread with the maximal outer diameter.

According to an embodiment, the threaded portion of the shaft may comprise a sub-portion with a first circumferential section without threads and a second circumferential section with threads. The first circumferential section may have an outer diameter corresponding to a minor diameter of the thread. The first circumferential section may extend on at least a third of the circumference of the sub-portion. A smooth transition may be provided in a circumferential direction between the first and second circumferential sections.

According to an embodiment, the thread may have a minimal diameter adjacent to the tip, which minimal diameter may for example be half of the maximal diameter. The tip may have rounded edges. The tip may have a part-spherical shape. Further, the tip may have a blunt end with rounded edges as smooth transition to the first turn of the thread.

According to an embodiment, a clearance groove may be provided on the shaft adjacent the head of the end cap, i.e. between the thread and the head. In the clearance groove, a chamfer may be provided as a transition between the root of the clearance groove and a radially outwardly extending surface of the head.

According to an embodiment, the head portion of the end cap may have an outer diameter which is substantially greater than the maximal outer diameter of the thread so as to form a circumferentially extending surface for abutment of the head against, for example, a proximal end surface of a bone nail. For example, the outer diameter of the head portion may be 1.5 to 1.7 times greater than the maximal outer diameter of the thread.

According to another embodiment, the shaft of the end cap may further comprise a portion without thread between the threaded portion and the head of the end cap, wherein the unthreaded portion has a diameter being greater than a maximal diameter of the threaded portion. Preferably, the diameter of the unthreaded portion is only slightly greater than the maximal diameter of the threaded portion. For example, the diameter of the unthreaded portion is 1.1 to 1.2 times greater than the maximal outer diameter of the threaded portion.

Alternatively, the head portion may also have a diameter being similar to the maximal diameter of the threaded portion so that the head portion may be inserted into the end portion of a bone nail. In such a case, an end surface of the end cap may be arranged so as to be flush with the end surface of the bone nail, when the end cap is screwed into the nail. Also here, the diameter of the head portion may be 1.1 to 1.2 times greater than the maximal outer diameter of the threaded portion.

Either the unthreaded portion or the head portion with the diameter being similar to the maximal diameter of the threaded portion, may fit into an unthreaded portion of a bore at an end of an intramedullary nail. Having a close fit between the bore in the nail and the end cap, provides the advantage that bone growing into the nail end may be reliably prevented, thus facilitating an extraction of the bone nail when the bone fracture is successfully treated by the bone nail.

According to an embodiment, a system may comprise an end cap according to any of the above described embodiments, and a bone nail with an inner thread for receiving the end cap. The system may further be provided with an aiming or targeting device for assisting an introduction of a locking screw and/or with a driving tool for manipulating the bone nail during an implantation of the same.

An exemplary bone nail may be an intramedullary nail comprising a through bore for receiving a locking screw, the through bore extending through the shaft of the bone nail in a direction transverse and possibly also inclined relative to a longitudinal axis of the shaft. The intramedullary nail may further comprise a bore formed at least in the trailing end section of the nail, with the bore extending in a longitudinal direction of the shaft of the nail, the longitudinal bore including an inner thread for releasably fixing a medical device like a driving tool for manipulating the implant during an implantation or like a targeting device, wherein the inner thread is also adapted to receive an end cap in accordance with the invention.

When used with an intramedullary nail, the end cap may further be configured to be a fixation means for a locking screw. The tip of the end cap may be in contact with an outer surface of the shaft of the locking screw within a bone nail, when being inserted into a trailing end of a bone nail. Thus, the end cap allows reducing any pain which may be caused by sharp edges at the trailing end of the implant and preventing any movement of a locking screw relative to the bone nail.

It has to be noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention as defined by the appended claims will now be described in detail with reference to the figures, it is done so in connection with the illustrative embodiments and is not limited by the particular embodiments illustrated in the figures.

DETAILED DESCRIPTION

Figure 3A:
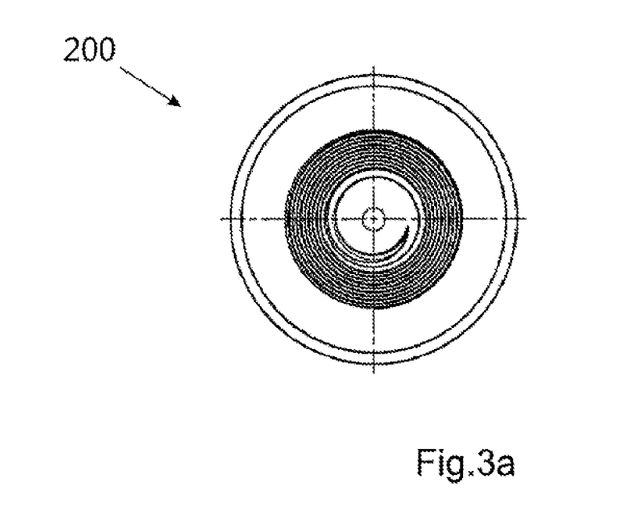
FIGS. 3a and 3b show an end cap according to a first embodiment.
Figure 3B:
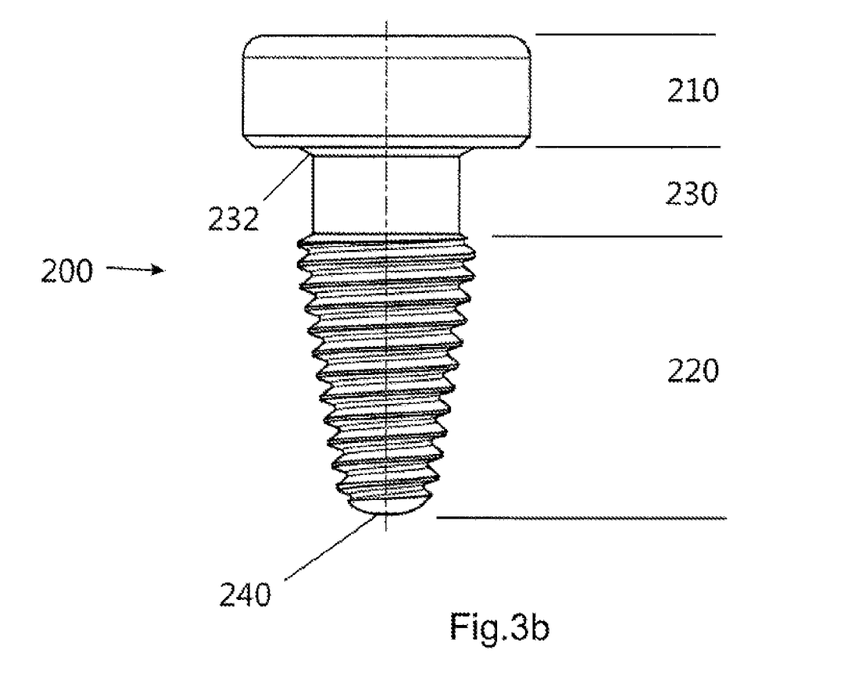

In FIGS. 3a and 3b, an end cap 200 according to a first embodiment is shown, with FIG. 3a being a view onto the tip 240 of the end cap 200, i.e. with a viewing direction from the bottom to the top of FIG. 3b.

The end cap 200 comprises a head 210, a conical portion 220, a clearance groove 230 as well as a tip 240. In this embodiment, the conical portion 220 is completely formed with a thread at the outer surface thereof. As a transition between the clearance groove 230 and the head 210, a chamfer 232 is provided.

Figure 4:
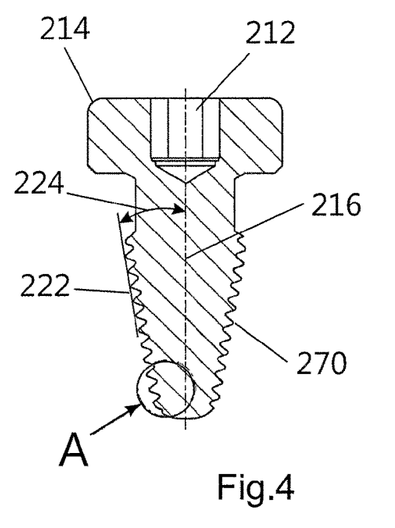
FIG. 4 is a section view of the end cap of FIGS. 3a, 3b including a detailed view of the thread.

As shown in FIG. 4, the head portion 210 of the end cap 200 comprises an inner tool engagement portion 212 as well as rounded edges 214. The conical portion may be described by an outer surface 222 which is inclined by an angle 224 relative to a longitudinally extending central axis 216 of the end cap 200. Threads 270 are cut into the outer surface 222.

Figure 4A:
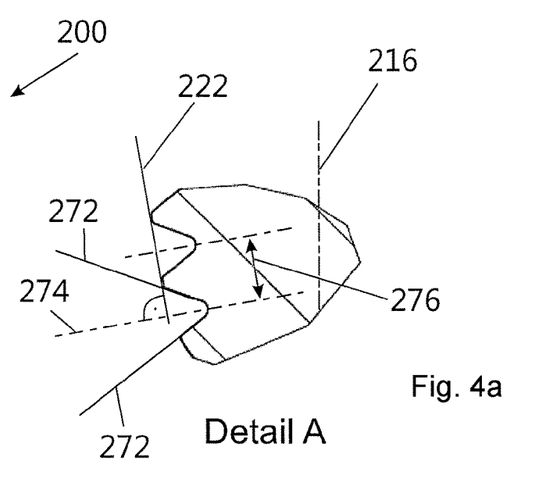
FIG. 4a is an enlarged view of detail A of FIG. 4.

Detail A is an enlarged view of the threads 270. In this embodiment, the threads are cut into the outer surface 222 of the conical portion so as to form two flanks 272. Between the flanks 272, a bisecting line 274 can be defined which is orientated perpendicularly to the outer surface 222. The threads 270 comprise a pitch 276, i.e. a distance between two turns of the threads, which is constant over the length of the threads.

Figures 5A, 5B, 5C, 5D:
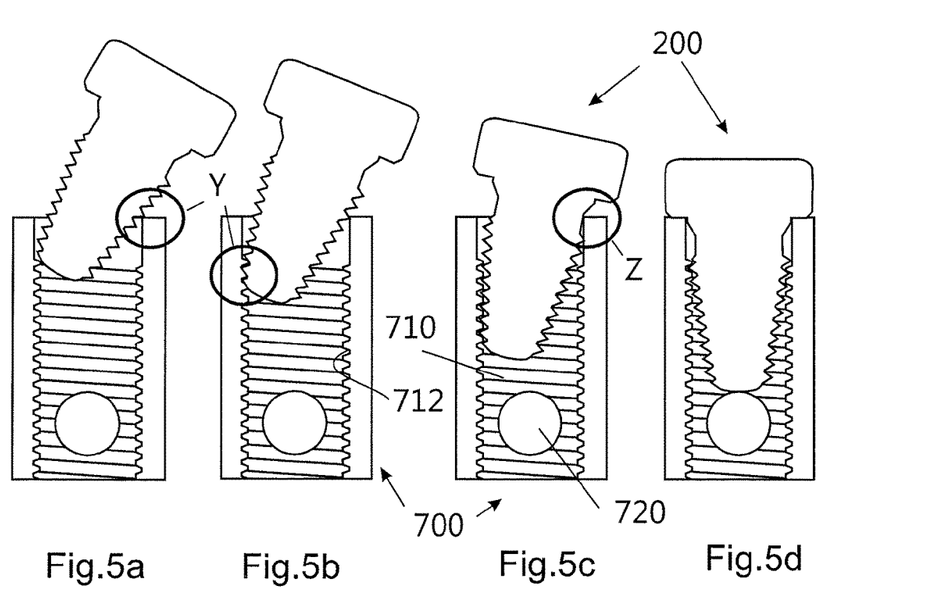
FIGS. 5a-5d show a sequence illustrating an introduction of an end cap of FIGS. 3a, 3b, 4 into a trailing end of a bone nail.

An introduction of an end cap 200 into a trailing end of a bone nail 700 is illustrated by the sequence shown in FIGS. 5a-5d. Assuming that the end cap 200 will be initially inserted into the trailing end of the bone nail 700 in a tilted direction or orientation, as shown in FIG. 5a, the threads on the conical portion of the end cap 200 will engage an edge at the trailing end of the bone nail 700 and/or the first turns of the threads 710 within a bore 712 in the bone nail 700, as indicated by the circle denoted with Y. The conical thread 270 allows screwing in the end cap 200 into the inner threads 710, although the axis 216 of the end cap 200 is inclined relative to the central axis of the bore 712 of bone nail 700, as shown in FIG. 5c. The axis 216 of the end cap 200 will be aligned automatically with the axis of bore 712 of the bone nail 700 by the chamfer 232 provided beneath the head 210 of the end cap, as indicated by the circle denoted with Z in FIG. 5c. Finally, the axis 216 of the end cap will be aligned with the axis of the bore 712 and at least the turn of the outer thread with the maximum diameter will engage the inner threads 710 in the bone nail trailing end.

As shown in FIG. 5d, the end cap 200 may have a length along axis 216 which corresponds to the distance between the trailing end and a first transverse through bore 720 in the bone nail 700. Therefore, the end cap 200 may be configured to be in contact with an outer surface of a locking screw (not shown), when the locking screw is inserted through the through bore 720 and the end cap is completely introduced into the trailing end of the bone nail 700, thus fixing the locking screw within the through bore.

Figure 6A:
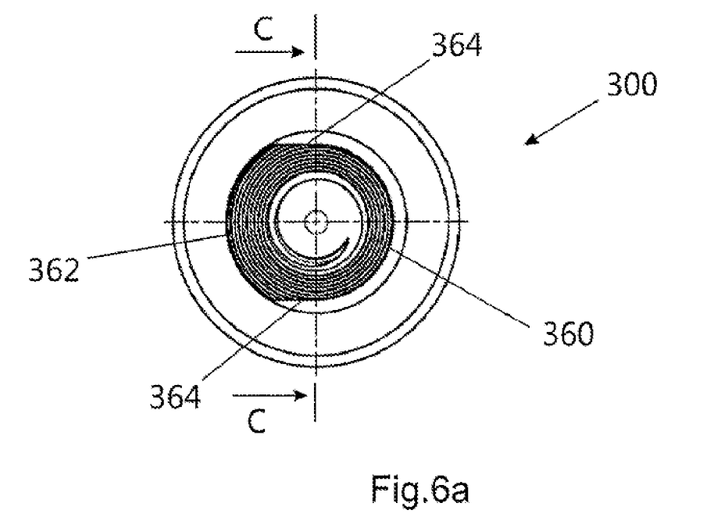
FIGS. 6a and 6b show an end cap according to a second embodiment.
Figure 6B:
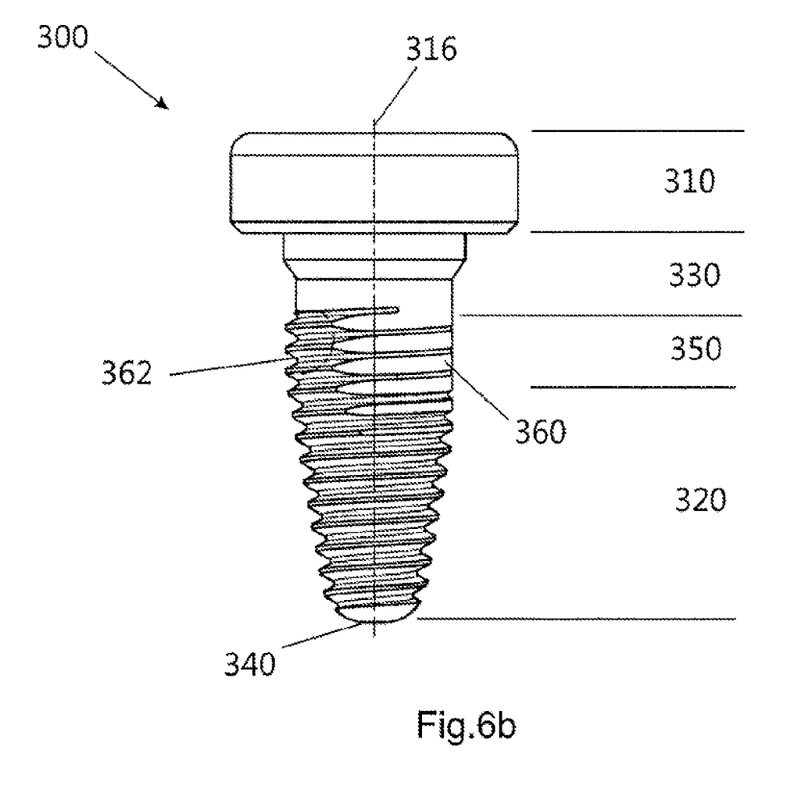

In FIGS. 6a and 6b, an end cap 300 according to a second embodiment is shown, with FIG. 6a being a view onto the tip 340 of the end cap 300.

The end cap 300 comprises a head 310, a conical portion 320, a clearance groove 330 as well as a tip 340, with the conical portion 320 being completely formed with a thread at the outer surface thereof. The end cap 300 further comprises a sub-portion 350. The threads on the conical portion 320 continue over the sub-portion 350, wherein the sub-portion 350 is cylindrically formed, thus having threads with a constant diameter.

Furthermore, the sub-portion includes a first circumferential section 360 without threads and a second circumferential section 362 with threads.

Figure 7:
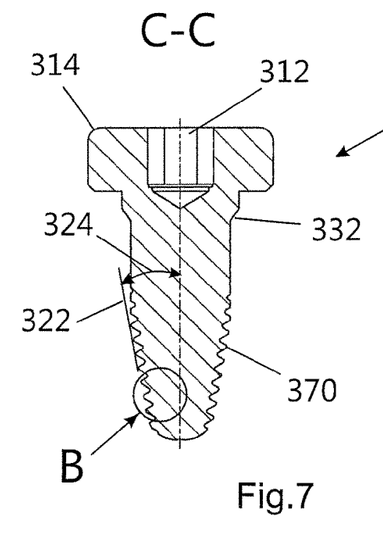
FIG. 7 is a section view of the end cap of FIGS. 6a, 6b including a detailed view of the thread.

As shown in FIG. 7 which is a section view along the section plane C-C as indicated in FIG. 6a, the head portion 310 of the end cap 300 comprises an inner tool engagement portion 312 as well as rounded edges 314. The conical portion may be described by an outer surface 322 which is inclined by an angle 324 relative to a longitudinally extending central axis 316 of the end cap 300.

Threads 370 of the end cap 300 may be generated by firstly cutting threads continuously into the outer surface of the conical portion 320 and into the outer surface of the sub-portion 350, and then removing the threads in the first circumferential section 360 by reducing the outer diameter in this section.

For example, the circumferential section 360 may form 50% of the circumference of the shaft portion and 80% to 100% of the threads may be removed in this section by machining, like for example by grinding or milling. When machining the threads, the shaft may be moved linearly from a side to a machining tool, may then be rotated for 180° about its axis, and may then be moved linearly again and sidewardly away from the machining tool. By way of such process, a circumferential section 360 with two opposite transition sections 364 may be formed, as shown in FIG. 6a, with the transition sections 364 forming a smooth transition from the first circumferential section 360 without threads to the second circumferential section 362 with threads.

Figure 7A:
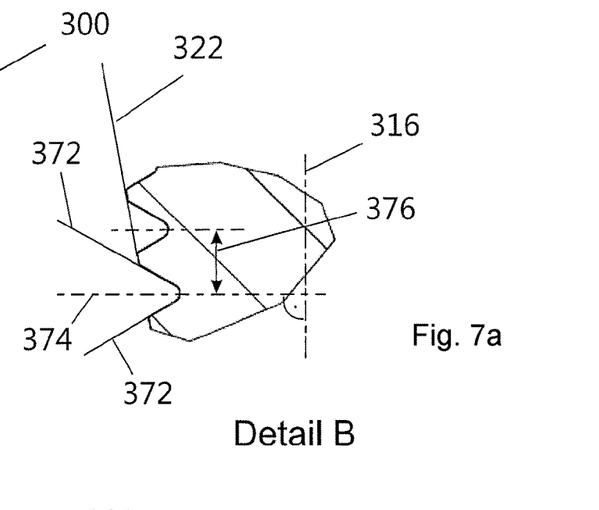
FIG. 7a is an enlarged view of detail B of FIG. 7.

Detail B is an enlarged view of the threads 370. In this embodiment, the threads are cut into the outer surface 322 of the conical portion so as to form two flanks 372, between which a bisecting line 374 can be defined which is orientated perpendicularly to the axis 316 of the end cap 300. The threads 370 comprise a pitch 376 which is constant over the length of the threads.

Figure 8A:
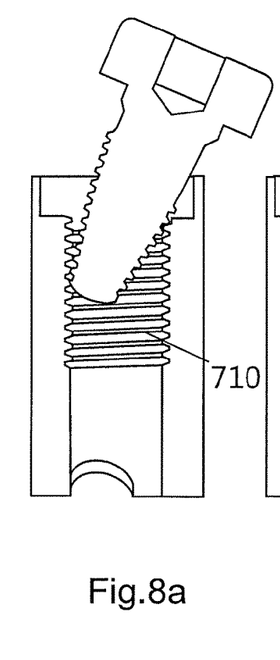
FIGS. 8a-8d show a sequence illustrating an introduction of an end cap of FIGS. 6a, 6b, 7 into a trailing end of a bone nail.
Figures 8B, 8C:
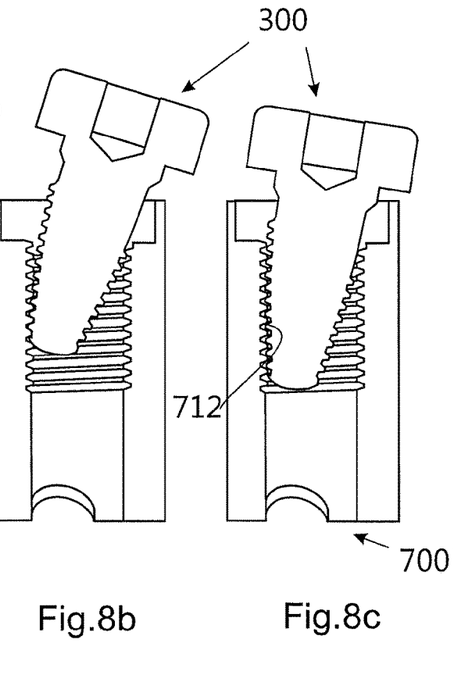

An introduction of an end cap 300 into a trailing end of a bone nail 700 is illustrated by the sequence shown in FIGS. 8a-8d. Also here, assuming that the end cap 300 will be initially inserted into the trailing end of the bone nail 700 in a tilted orientation, as shown in FIG. 8a, the threads 370 on the conical portion of the end cap 300 will engage at least an edge at the trailing end of the bone nail 700 and/or the first turns of the threads 710 within the bore 712 of bone nail 700. The conical thread 370 allows screwing in the end cap 300 into the inner threads 710, although the axis 316 of the end cap 300 is inclined relative to the axis of the bone nail 700, as shown in FIGS. 8b and 8c. The axis of the end cap 300 will be aligned automatically with the central axis of the bore 712 of the bone nail 700 when screwing in the end cap.

Figure 8D:
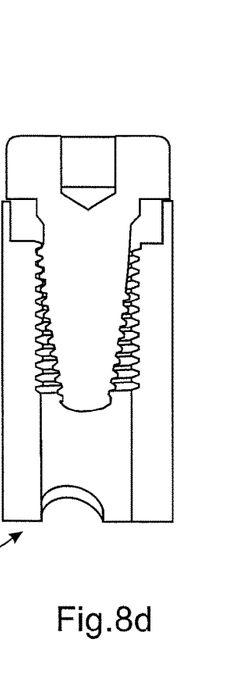

As soon as the end cap 300 is completely introduced into the bone nail 700, the turns of the outer thread at the second circumferential section 362 of the sub-portion 350 will engage the inner threads 710 in the bone nail and the axis 316 of the end cap will finally be aligned with the central axis of bore 712 of the bone nail.

As long as the end cap axis 316 is not aligned with the axis of the bone nail, while screwing in the end cap 300, the first circumferential section 360 without threads will prevent any clamping of the threads. With regard to end cap 200 or 300, the diameter of the threads 270, 370 at the conical portion of the end cap 200, 300 is smaller than the diameter of the inner threads 710 in the bone nail 700, and with regard to end cap 300, the thread 370 is provided in a cylindrical portion of the shaft only on one side, so as to avoid an asynchronous engagement of threads on opposite sides, i.e. to avoid for example an engagement of one turn of the outer thread into two different turns of the inner thread on opposite sides.

Figure 9A:
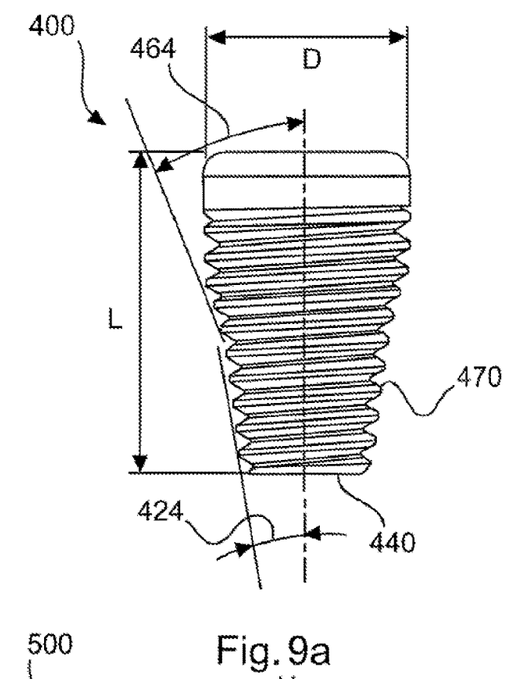
FIGS. 9a and 9b show an end cap according to a third embodiment.
Figure 9B:
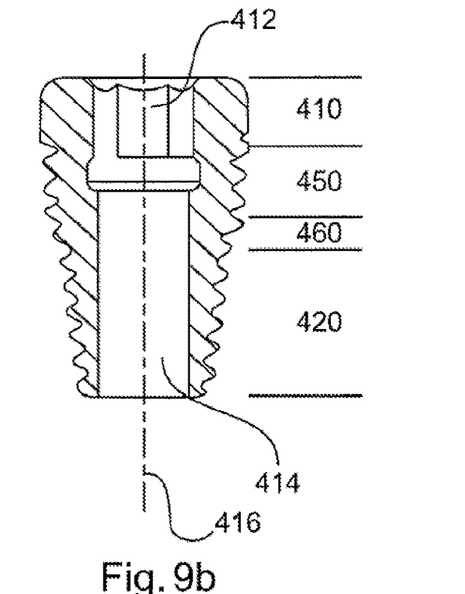

In FIGS. 9a and 9b, an end cap 400 according to a third embodiment is shown, with FIG. 9a being a side view and FIG. 9b being a section view of the end cap 400.

The end cap 400 comprises a length L, with four sections along the length of the end cap. The end cap comprises a threaded portion with a first conical section 420, a second conical section 460 and a cylindrical section 450. The end cap further comprises a section 410 without a thread. The thread of the threaded portion is formed as a continuous thread with a constant pitch over the first conical section, the second conical section and the cylindrical section at the outer surface of the end cap. As the threads continue over the cylindrical section, the threads have a constant diameter there.

The first conical section 420 may be described by a cone which is inclined by an angle 424 relative to a longitudinally extending central axis 416 of the end cap 400. The second conical section 460 may be described by a cone which is inclined by an angle 464 relative to the longitudinal axis 416.

As shown in FIG. 9b which is a section view along a centre plane of the end cap, the end cap 400 further comprises an inner tool engagement portion 412 as well as a through bore 414 in axial direction of the end cap. The diameter D of the unthreaded section 410 which may also be denoted as head portion is slightly greater than the maximal outer diameter of the thread in section 450 of the threaded portion.

The length of the first conical section 420 may be between 0.35 L and 0.55 L, the length of the second conical section 460 may be between 0.05 L and 0.15 L, the length of the cylindrical section 450 may be between 0.1 L and 0.25 L, and the length of the head portion 410 may be the remainder of L.

According to an example, the first conical section 420 may have a diameter of 5.5 mm at the tip of the end cap, a cone angle of 7.125°, and a length of 6 mm, so that the diameter between the first and second conical sections may be 6.8 mm. The second conical section 460 may have a cone angle of 22.5° and a length of only 1.5 mm, with a maximal diameter at the transition to the cylindrical section of 8 mm. The length of the cylindrical section 450 may be 2.5 mm and the length of the unthreaded head portion 410 may be 3 mm. Consequently, the total length L of the end cap 400 according to this example may be 13 mm. Further, the thread may be a metric thread denoted as M8x1, wherein a skilled person will understand that the nominal diameter of the thread of 8 mm will be realized only on the cylindrical section 450, whereas the pitch is intended to be constant over the complete length of the threaded portion. The head portion 410 may have an outer diameter D of 8.2 mm.

Figure 10A:
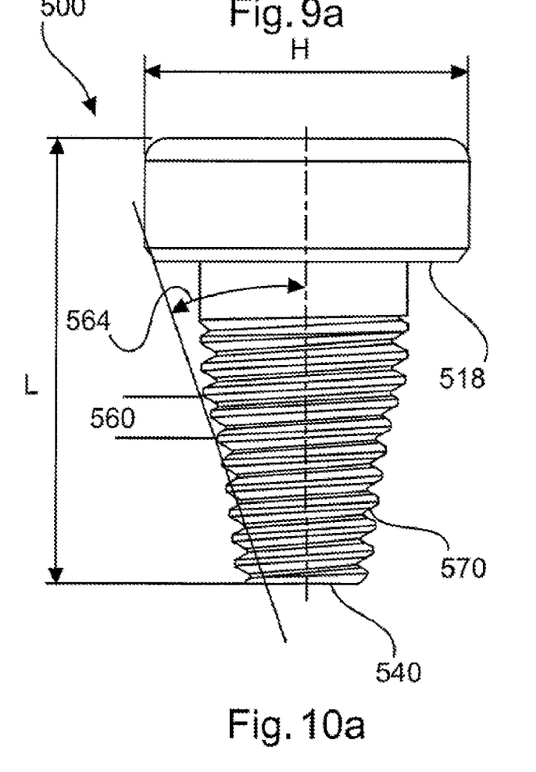
FIGS. 10a and 10b show an end cap according to a fourth embodiment.
Figure 10B:
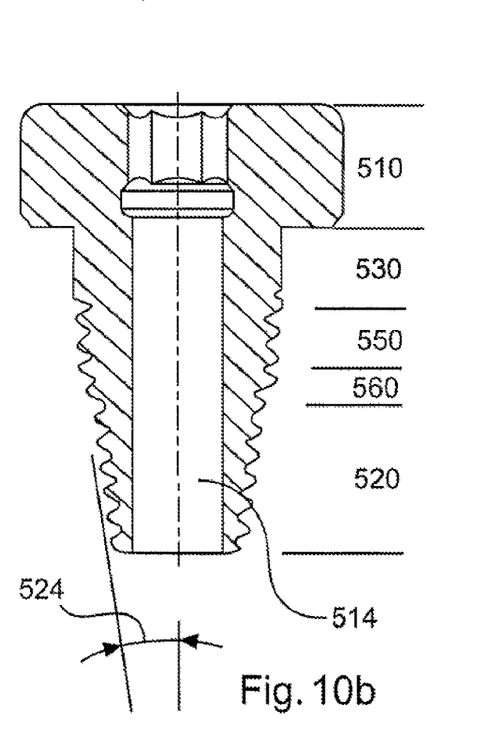

In FIGS. 10a and 10b, an end cap 500 according to a fourth embodiment is shown, with FIG. 10a being a side view and FIG. 10b being a section view of the end cap 500.

The end cap 500 comprises a tip 540, a first conical section 520 with a first cone angle 524, a second conical section 560 with a second cone angle 564, a cylindrical section 550, an unthreaded section 530 as well as a head portion 510. The head portion includes a surface 518 which faces towards the threaded portion and which extends perpendicular to the longitudinal axis 516. The surface 518 will abut for example at an end face of a bone nail, when the end cap is inserted into the nail and engages an inner thread of the same.

The end cap 500 according to the fourth embodiment can be seen as a combination of the previously described embodiments, with the threaded portion of the third embodiment and the head portion as well as the unthreaded portion of the second embodiment. The concrete form of the thread of end cap 500 may be as described above in connection with FIG. 4, detail A or FIG. 7, detail B. Furthermore, the end cap 500 may or may not have a clearance groove in the unthreaded section, but may preferably have a diameter in the unthreaded section 530 which is slightly larger than the outer diameter of the thread.

In particular, the end cap 500 can be seen as an end cap 400 having additionally a head portion. Thus, the total length L of the end cap 500 may be 18 mm, i.e. a head portion with a length of 5 mm together with a 13 mm shaft like that described with respect to the end cap 400. The outer diameter H of the head portion 510 may be 13 mm.

With respect to an introduction of an end cap according to both the third and fourth embodiment, it is referred to the description of FIGS. 5 and 8, respectively. The end cap may be inserted into a bore in an end of an intramedullary nail with a tilted orientation, and may nevertheless be easily screwed in. Upon engagement of the threaded and conical portion of the end cap with an inner thread in the bore in the nail, and upon rotation of the end cap, the end cap will automatically find its correct position and orientation within the end of the nail.

FIG. 11 is an image showing circumstances under which a surgeon may insert an end cap 100, 200, 300, 400, 500 into a trailing end of a bone nail 600, 700. With the end cap at the end of the tool 800, the end cap 100, 200, 300, 400, 500 may be inserted into the trailing end of the bone nail, wherein only a small part of the bone as well as of the bone nail is visible so that the actual orientation of the axis of the bone nail cannot be seen. Furthermore, the insertion of the end cap 100, 200, 300, 400, 500 is difficult as the surrounding soft tissue provides less space to manipulate the tool 800. The invention proposes an end cap an insertion of which is facilitated.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

LIST OF REFERENCE SIGNS 100, 200, 300, 400, 500 end cap
110, 210, 310, 410, 510 head/head portion
212, 312, 412, 512 inner tool engagement portion
214, 314 rounded edges
414, 514 through bore
216, 316, 416, 516 centre axis
120, 220, 320, 420, 460, 520, 560 cone/conical portion/conical section
222, 322 outer surface
224, 324, 424, 464, 524, 564 cone angle
130 intermediate portion
131 clearance groove
132, 232, 332 shoulder, chamfer
240, 340, 440, 540 tip
150 threaded portion
350, 450, 550 cylindrical section, sub-portion
360 first circumferential section
362 second circumferential section
364 transition section
270, 370 threads
272, 372 flanks
274, 374 bisecting line
276, 376 pitch
600, 700 bone nail
610, 710 inner threads
712 longitudinal bore
720 through bore
800 tool

The invention claimed is:

1. An end cap for use with an intramedullary nail, comprising:
a head portion with a tool engagement portion;
a shaft with a longitudinal axis and a tip, wherein a thread with a constant pitch is provided on at least a portion of the shaft;
wherein the threaded portion of the shaft comprises a first end adjacent the tip of the shaft, a first conical section, a second conical section and a second end, wherein the first conical section extends between the first end and the second conical section; and
wherein the first conical section defines a first cone with a first angle between its cone surface and the longitudinal axis, the first conical section having a first thread turn and a second thread turn aligned with the first angle, and the second conical section defines a second cone with a second angle between its cone surface and the longitudinal axis, the second conical section having a third thread turn and a fourth thread turn aligned with the second angle, wherein the first angle differs from the second angle,
wherein a first distance perpendicular to the longitudinal axis is defined between a major diameter of the first thread turn and a major diameter of the second thread turn of the first conical section and a second distance perpendicular to the longitudinal axis is defined between a major diameter of the third thread turn and a major diameter of the fourth thread turn of the second conical section, the first distance being less than the second distance.

2. The end cap of claim 1, wherein the first angle of the first conical section is smaller than the second angle of the second conical section.

3. The end cap of claim 1, wherein the threaded portion comprises a further section between the second conical section and the second end of the threaded portion, wherein the further section of the threaded portion is cylindrical.

4. The end cap of claim 1, wherein the threaded portion comprises a further section between the second conical section and the second end of the threaded portion, wherein the further section of the threaded portion defines a third cone with a third angle between its cone surface and the longitudinal axis, wherein the third angle differs from the first angle and differs from the second angle.

5. The end cap of claim 1, wherein the first angle is between 5° and 10° and the second angle is between 20° and 25°.

6. The end cap of claim 1, wherein the thread has a maximal diameter adjacent to the head portion, which diameter corresponds to a nominal diameter of an inner thread of a bone nail.

7. The end cap of claim 1, wherein the shaft of the end cap further comprises a section without thread between the threaded portion and the head of the end cap, wherein the unthreaded section has a diameter being greater than a maximal diameter of the threaded portion.

8. The end cap of claim 1, wherein a diameter of the head portion is similar to a maximal diameter of the threaded portion.

9. The end cap of claim 1, wherein the tip has rounded edges.

10. The end cap of claim 1, wherein the tool engagement portion is an inner tool engagement portion.

11. The end cap of claim 1, further comprising a sub-portion having a circumferential section without thread formed in the threaded portion of the shaft, wherein the circumferential section has an outer diameter corresponding to a minor diameter of the thread and extends on at least a third of a circumference of the sub-portion.

12. A system comprising:
an end cap of claim 1; and
a bone nail with an inner thread for receiving the end cap.

13. The system of claim 12, further comprising a locking screw, wherein the bone nail further comprises a transverse bore for receiving the locking screw, wherein the end cap is configured to be in contact with the locking screw, when the locking screw is inserted in the transverse bore of the bone nail and when the end cap is inserted into the inner thread of the bone nail.

14. An end cap for use with an intramedullary nail comprising:
a first end with a tool engagement structure and a second end;
a first threaded conical section and a second threaded conical section extending between the first and second ends, the first conical threaded section adjacent the second end of the end cap and the second threaded conical section extending from the first threaded conical section towards the first end of the end cap, the first and second threaded conical sections having different cone angles with the cone angle of the first threaded conical section being less than the cone angle of the second threaded conical section, the first threaded conical section having at least two first thread turns aligned with the cone angle of the first threaded conical section, and the second threaded conical section having at least two second thread turns aligned with the cone angle of the second threaded conical section.

15. The end cap of claim 14 further comprising a third threaded section located between the second threaded conical section and the first end of the end cap, the third threaded section having a cylindrical thread.

16. The end cap of claim 14, wherein the threaded portion comprises a further section between the second conical section and the second end of the threaded portion, wherein the further section of the threaded portion defines a third cone with a third angle between its cone surface and the longitudinal axis, wherein the third angle differs from the first angle and differs from the second angle.

17. The end cap of claim 14, wherein the first angle is between 5° and 10° and the second angle is between 20° and 25°.

18. The end cap of claim 14, further comprising a shaft having a section without thread between the threaded portion and the head of the end cap, wherein the unthreaded section has a diameter being greater than a maximal diameter of the threaded portion.

19. The end cap of claim 14, wherein a diameter of the head portion is similar to a maximal diameter of the threaded portion.

20. The end cap of claim 14, wherein the tool engagement portion is an inner tool engagement portion.

* * * * *